US011957373B2

(12) United States Patent
Jezierski et al.

(10) Patent No.: US 11,957,373 B2
(45) Date of Patent: Apr. 16, 2024

(54) SYSTEMS AND METHODS OF DETERMINING ORIENTATION OF CUTTING WINDOWS OF A MECHANICAL RESECTION INSTRUMENT

(71) Applicants: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

(72) Inventors: Rafal Z. Jezierski, Candia, NH (US); Peter M. Cesarini, Londonderry, NH (US); Christopher D. McDonald, Newburyport, MA (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 418 days.

(21) Appl. No.: 17/315,840

(22) Filed: May 10, 2021

(65) Prior Publication Data
US 2021/0353321 A1  Nov. 18, 2021

Related U.S. Application Data

(60) Provisional application No. 63/023,473, filed on May 12, 2020.

(51) Int. Cl.
*A61B 17/32* (2006.01)
*A61B 17/00* (2006.01)
(Continued)

(52) U.S. Cl.
CPC ........ *A61B 17/32002* (2013.01); *A61B 34/20* (2016.02); *A61B 2017/00039* (2013.01);
(Continued)

(58) Field of Classification Search
CPC ...... A61B 17/32002; A61B 17/320783; A61B 17/00039; A61B 17/00876; A61B 34/20; A61B 2034/2051; A61B 2090/0811
See application file for complete search history.

(56) References Cited

U.S. PATENT DOCUMENTS 4,108,182 A  8/1978  Hartman et al.
5,376,078 A  12/1994  Dinger, III et al.
(Continued)

FOREIGN PATENT DOCUMENTS

GB  2491524 A  12/2012
WO  2018184034 A1  10/2018

*Primary Examiner* — Jocelin C Tanner
(74) *Attorney, Agent, or Firm* — Dickinson Wright PLLC; Mark E. Scott

(57) ABSTRACT

Determining orientation of cutting windows of a mechanical resection instrument. At least some of the example embodiments are methods including: sensing a location of a cutting window through an outer tube of the mechanical resection instrument, the sensing based on a magnetic field strength of a first magnet; sensing a location of a cutting window through an inner tube concentrically disposed within the outer tube, the sensing based on a combined magnetic field strength of the first magnet and a second magnet; and stopping a rotation of the inner tube relative to the outer tube with the cutting window through the outer tube and the cutting window through the inner tube in a predetermined orientation, the stopping based on the combined magnetic field strength.

17 Claims, 8 Drawing Sheets

(51) Int. Cl.
 *A61B 17/3207* (2006.01)
 *A61B 34/20* (2016.01)
(52) U.S. Cl.
 CPC ............... *A61B 17/320783* (2013.01); *A61B 2034/2051* (2016.02)

(56) References Cited

U.S. PATENT DOCUMENTS

| | | |
|---|---|---|
| 5,592,727 A | 1/1997 | Glowa et al. |
| 5,602,449 A | 2/1997 | Krause et al. |
| 5,810,858 A | 9/1998 | Berman et al. |
| 8,568,418 B2 | 10/2013 | Matusaitis et al. |
| 8,702,702 B1 | 4/2014 | Edwards et al. |
| 9,649,123 B2 | 5/2017 | Riva |
| 9,872,695 B2 | 1/2018 | Riva |
| 9,955,991 B2 | 5/2018 | Riva |
| 10,299,818 B2 | 5/2019 | Riva |
| 10,517,610 B2 | 12/2019 | Philipp et al. |
| 2011/0028790 A1 | 2/2011 | Farr et al. |
| 2012/0130380 A1 | 5/2012 | Babaev |
| 2013/0085498 A1* | 4/2013 | Matusaitis ........ A61B 17/32002 606/180 |
| 2015/0223897 A1 | 8/2015 | Kostrzewski et al. |
| 2017/0303990 A1 | 10/2017 | Benamou et al. |
| 2017/0360466 A1 | 12/2017 | Brown et al. |
| 2018/0228551 A1* | 8/2018 | Moe ....................... A61B 34/20 |
| 2019/0059983 A1 | 2/2019 | Germain et al. |
| 2019/0083121 A1 | 3/2019 | Benamou et al. |
| 2019/0134279 A1* | 5/2019 | Benamou ................. A61B 1/05 |
| 2019/0192180 A1 | 6/2019 | Germain et al. |
| 2019/0247068 A1 | 8/2019 | Whipple |
| 2019/0374278 A1 | 12/2019 | Malkevich et al. |
| 2019/0388117 A1* | 12/2019 | Akbarian .............. A61M 1/742 |
| 2020/0268405 A1 | 8/2020 | Prokop |
| 2022/0133394 A1 | 5/2022 | Benamou et al. |

\* cited by examiner

SYSTEMS AND METHODS OF DETERMINING ORIENTATION OF CUTTING WINDOWS OF A MECHANICAL RESECTION INSTRUMENT

CROSS-REFERENCE TO RELATED APPLICATIONS

This application claims the benefit of U.S. Prov. 63/023,473 filed May 12, 2020 and titled, "Systems and Methods of Determining Orientation of Cutting Windows of a Mechanical Resection Instrument." The provisional application is incorporated by reference herein as if reproduced below in full.

BACKGROUND

Mechanical resection devices are surgical tools used to cut or resect tissue. In many cases, the cutting and resection is based on turning a burr or blade that removes the tissue, and the resection device also comprises a channel through which the tissue pieces are aspirated away from the surgical site. For reasons of sterility, among others, the actual cutting instrument is usually a disposable, one-time use instrument. However, the handle or motor drive unit (MDU) held by the surgeon is reused from patient to patient, and sterilized between each use (e.g., autoclaved).

The MDU device may be used with many different types of resection devices, and may in fact be used with multiple resection devices within a single surgical setting. Each resection device may have its own operational parameters (e.g., speed of rotation of cutting elements, direction of rotational, or rotational mode such as oscillatory). Moreover, some resection devices can be coupled to the MDU in more than one orientation. The variations of mechanical resection devices and their respective operational parameters are communicated to the resection control unit for proper operation.

BRIEF DESCRIPTION OF THE DRAWINGS

For a detailed description of example embodiments, reference will now be made to the accompanying drawings (not necessarily to scale) in which.

DEFINITIONS

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various embodiments are directed to systems and methods of determining orientation of cutting windows of a mechanical resection instrument. More particularly, example embodiments are directed to sensing a location of a cutting window through an inner tube concentrically disposed within an outer tube, the sensing with respect to the inner tube based on a magnetic field strength of a magnet coupled to an inner hub of the mechanical resection instrument. Other example embodiments are directed sensing a location of a cutting window through an outer tube of a mechanical resection instrument based on reading a magnetic field strength of a first magnet associated with an outer hub of the mechanical resection instrument, and sensing a location of a cutting window through an inner tube concentrically disposed within the outer tube, the sensing with respect to the inner tube based on a combined magnetic field strength of the first magnet and a second magnet coupled to an inner hub of the mechanical resection instrument. Additionally, parameters of the mechanical resection instrument (e.g., type, speed of operation, operational mode) may be determined based on the magnetic field strengths, alone or in combination. The specification turns to example resection system to orient the reader.

Figure 1:
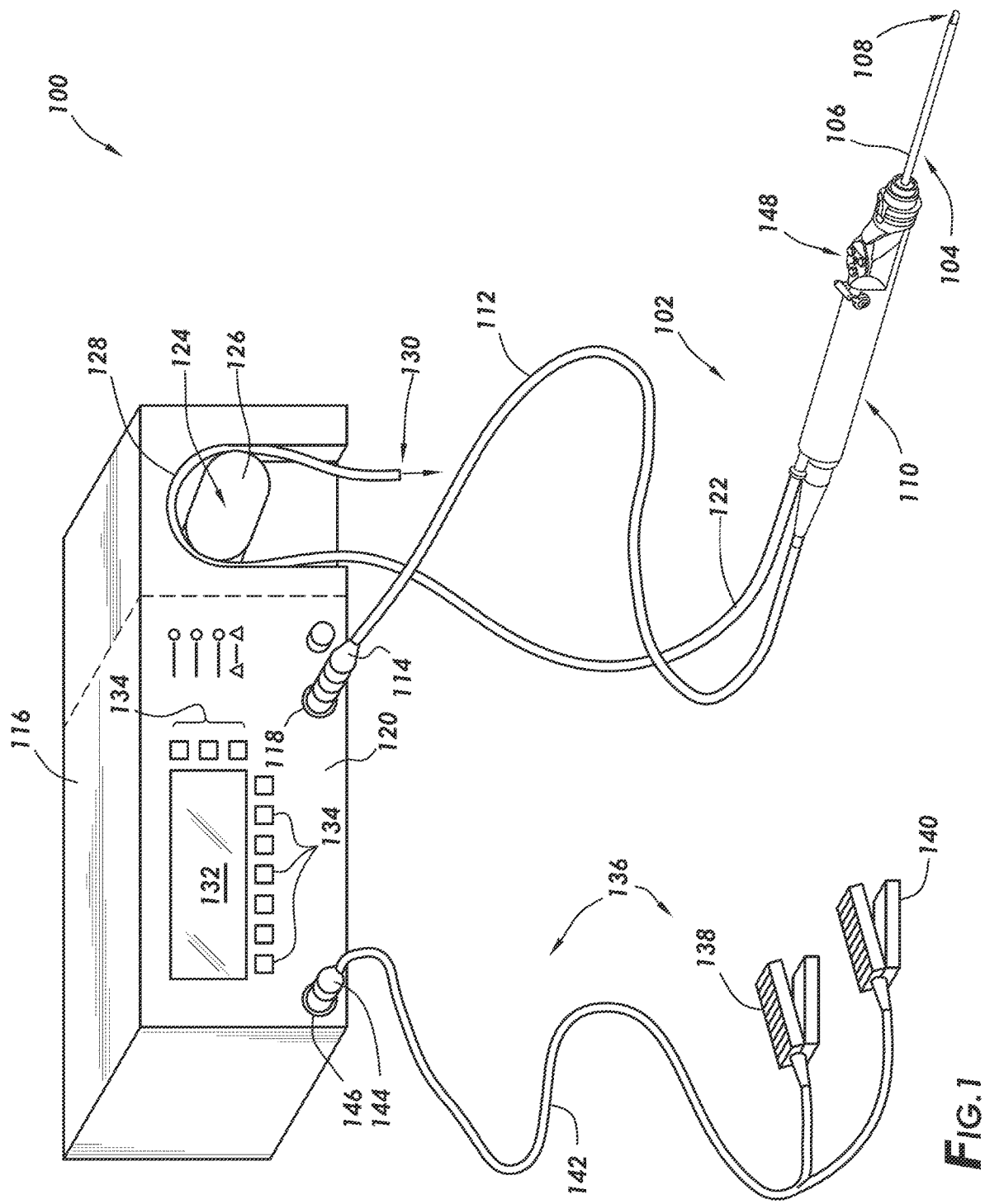
FIG. 1 shows a resection system in accordance with at least some embodiments.

FIG. 1 shows a mechanical resection system in accordance with at least some embodiments. In particular, the mechanical resection system 100 comprises a wand 102. The wand 102 includes a mechanical resection instrument 104 that comprises an elongate shaft 106 defining a distal end 108. Further, the wand 102 comprises a hand piece or motor drive unit (MDU) 110 where a physician grips the wand 102 during surgical procedures. The wand 102 further comprises a flexible multi-conductor cable 112 housing one or more electrical leads (not specifically shown), and the flexible multi-conductor cable 112 terminates in a wand connector 114. As shown in FIG. 1, the wand 102 is coupled to a resection control unit 116, such as by a controller connector 118 on an outer surface of the enclosure 120 (in the illustrative case of FIG. 1, the front surface of the enclosure 120).

Though not visible in the view of FIG. 1, in some embodiments the wand 102 has one or more internal aspiration channels or fluid conduits. The internal fluid conduit of the wand 102 is coupled to a flexible tubular member 122 used to provide suction or aspiration at the distal end 108 of the wand 102. In accordance with example embodiments, the flexible tubular member 122 couples to a peristaltic pump 124, which peristaltic pump 124 is illustratively shown as an integral component with the resection control unit 116 (i.e., residing at least partially within the enclosure 120 of the resection control unit 116). In other embodiments, an enclosure for the peristaltic pump 124 may be separate from the enclosure 120 for the resection control unit 116 (as shown by dashed lines in the figure).

The example peristaltic pump 124 comprises a rotor portion 126 (hereafter just "rotor 126") as well as a stator portion 128 (hereafter just "stator 128"). The flexible tubular member 122 is coupled within the peristaltic pump 124 between the rotor 126 and the stator 128, and movement of the rotor 126 against the flexible tubular member 122 causes fluid movement toward the discharge 130. While the illustrative peristaltic pump 124 is shown with a two-head rotor 126, other types of peristaltic pumps 124 may be used (e.g., a five-head peristaltic pump). In the context of the various embodiments, the peristaltic pump 124 creates a volume-controlled aspiration from a cavity or surgical field at the distal end 108 of the wand 102 (the surgical field not specifically shown), with the outflow rate based on a speed of the rotor 126, as commanded by the resection control unit 116. In other cases, the suction provided to the flexible tubular member 122 may be from any suitable source, such as wall suction provided within a hospital surgical room or recovery room.

Still referring to FIG. 1, a display device or interface device 132 is visible through the enclosure 120 of the resection control unit 116, and in some embodiments a user may select operational modes of the resection control unit 116 by way of the interface device 132 and related buttons 134. For example, using one or more of the buttons 134 the surgeon may select a rotational mode of the rotating portion of the mechanical resection instrument 104 (the rotating portion discussed more below). As another example, using one or more of the buttons 134 the surgeon may select an aggressiveness of the outflow control through the wand 102.

In some embodiments the mechanical resection system 100 also comprises a foot pedal assembly 136. The foot pedal assembly 136 may comprise one or more foot pedal devices 138 and 140, a flexible multi-conductor cable 142, and a pedal connector 144. While only two foot pedal devices 138 and 140 are shown, one or more pedal devices may be implemented. The enclosure 120 of the resection control unit 116 may comprise a corresponding connector 146 that couples to the pedal connector 144. A surgeon may use the foot pedal assembly 136 to control various aspects of the resection control unit 116. For example, foot pedal device 138 may be used for on-off control of a motor within the wand 102. Further, foot pedal device 140 may be used to control and/or set rotational mode of the rotating portion of the mechanical resection instrument 104. Alternatively, control of the various operational or performance aspects of the resection control unit 116 may be activated by selectively depressing the electrical switches or buttons 148 located on the MDU 110 of the wand 102.

Figure 2:
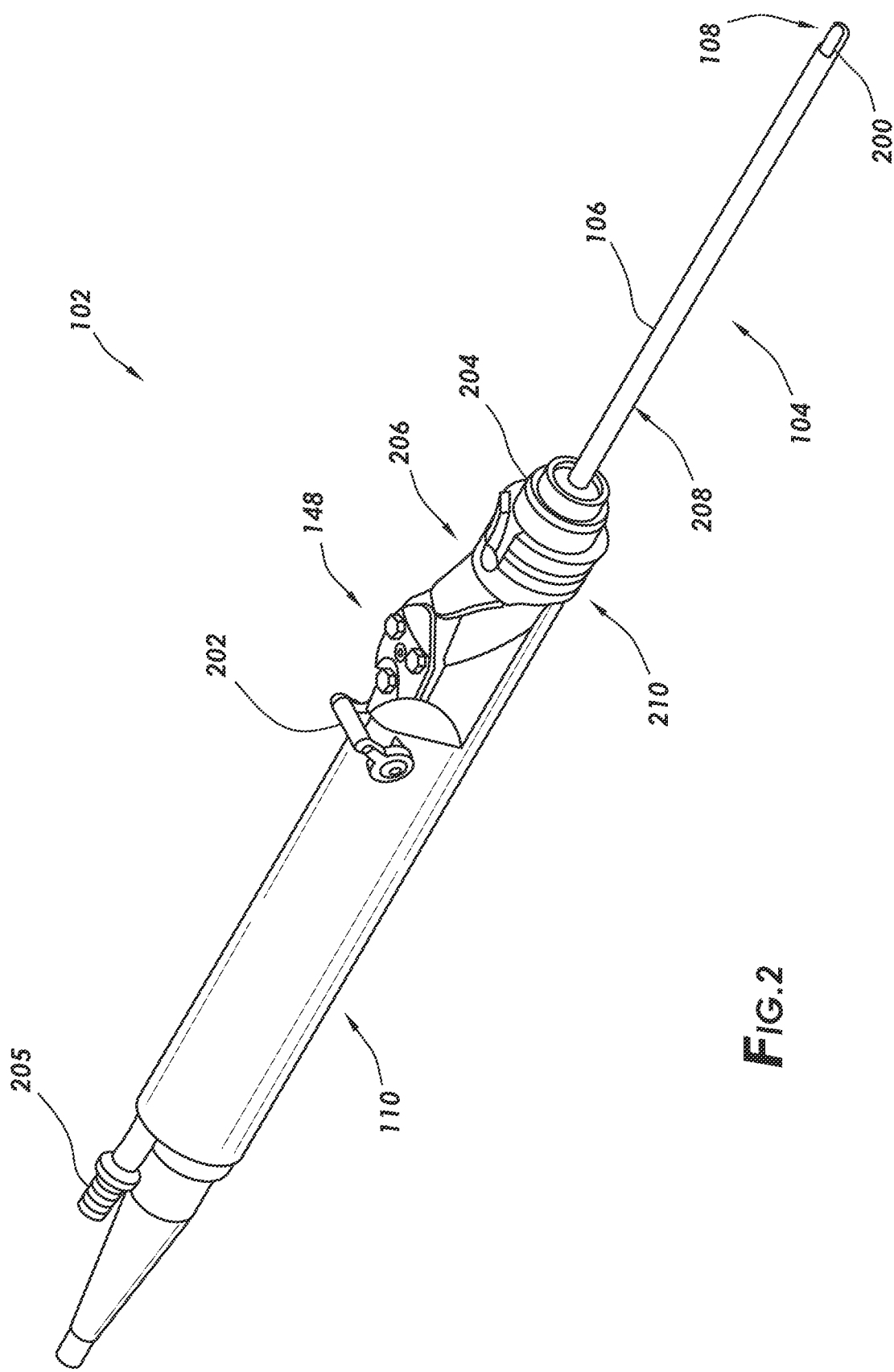
FIG. 2 shows a perspective view of a wand in accordance with at least some embodiments.

FIG. 2 shows a perspective view of a wand 102 in accordance with at least some embodiments. In particular, visible in FIG. 2 is the example MDU 110 as well as the example mechanical resection instrument 104. In the example wand 102 of FIG. 2, the mechanical resection instrument 104 is a blade-type device where the elongate shaft 106 is defined by an outer tube 208, and telescoped within the outer tube is an inner tube (not visible in FIG. 2). At the distal end 108 a cutting window 200 is provided through the outer tube 208. The inner tube, though not visible, is telescoped within and concentrically disposed within the outer tube 208, and the inner tube has a corresponding cutting window. When the cutting windows of the inner tube and outer tube 208 align, tissue is drawn into the cutting window 200, and the interaction of cutting surfaces of the outer tube 208 and inner tube cuts the tissue. In the case of the mechanical resection instrument being a blade-type device, suction provided by the peristaltic pump 124 or other vacuum source draws fluid and resection byproducts through the outer tube 208; and more particularly, the peristaltic pump 124 or other vacuum source draws fluid and resection byproducts through the inside diameter of the inner tube.

Also visible in FIG. 2 are the buttons 148 that the surgeon may use to control various aspects of the operation of the wand 102 (e.g., speed of rotation of the inner tube, direction of rotation, rotational mode, aggressiveness of aspiration through the wand 102). FIG. 2 further shows that the MDU 110 may implement a suction lever 202. The suction lever 202 is rotationally coupled to an outside surface of the MDU 110. The suction lever 202 is attached to a valve member (not shown in FIG. 2) within the MDU 110. More specifically, the valve member is disposed within a flow channel defined within the MDU 110, and the flow channel is fluidly coupled to the hose connector 205. In most cases, the suction lever 202 (and thus the internal valve member) is placed in a fully open position and remains in a fully open position during use, but is available to the surgeon for modulation of the suction through the wand 102.

In many cases, the mechanical resection instrument 104 is a single-use item that is used for a particular surgical procedure, and then discarded. By contrast, the MDU 110 may be cleaned, sterilized, and reused for multiple surgical procedures. Many different mechanical resection instruments may be coupled to the MDU 110 (and thus coupled to the resection control unit 116 (FIG. 1)). The different mechanical resection instruments include not only the categories of blade-type and burr-type devices, but also variations within each category. For example, there may be many blade-type devices from which a surgeon may choose, such as blade-type devices having varying outside diameters of the elongate shaft 106, varying axial lengths of the elongate shaft 106 (i.e., lengths measured parallel to a longitudinal axis through the inside diameter of the outer tube that defines the elongate shaft 106), and varying aggressiveness of cutting surfaces (e.g., smooth, toothed). Regardless of the mechanical resection instrument selected (and, in fact, multiple can be used in any one surgical procedure), each mechanical resection instrument 104 includes a coupler or outer hub 204 designed and constructed to couple to a hub connector 210 on a distal end 206 of the MDU 110. When the outer hub 204 is mechanically coupled to the hub connector 210 of the MDU 110, the flow pathway within the mechanical resection instrument 104 is fluidly coupled to the flow channel through the MDU 110, and the rotating portion (e.g., an inner hub and the inner tube) of the mechanical resection instrument is mechanically coupled to the motor within the MDU 110.

Figure 3:
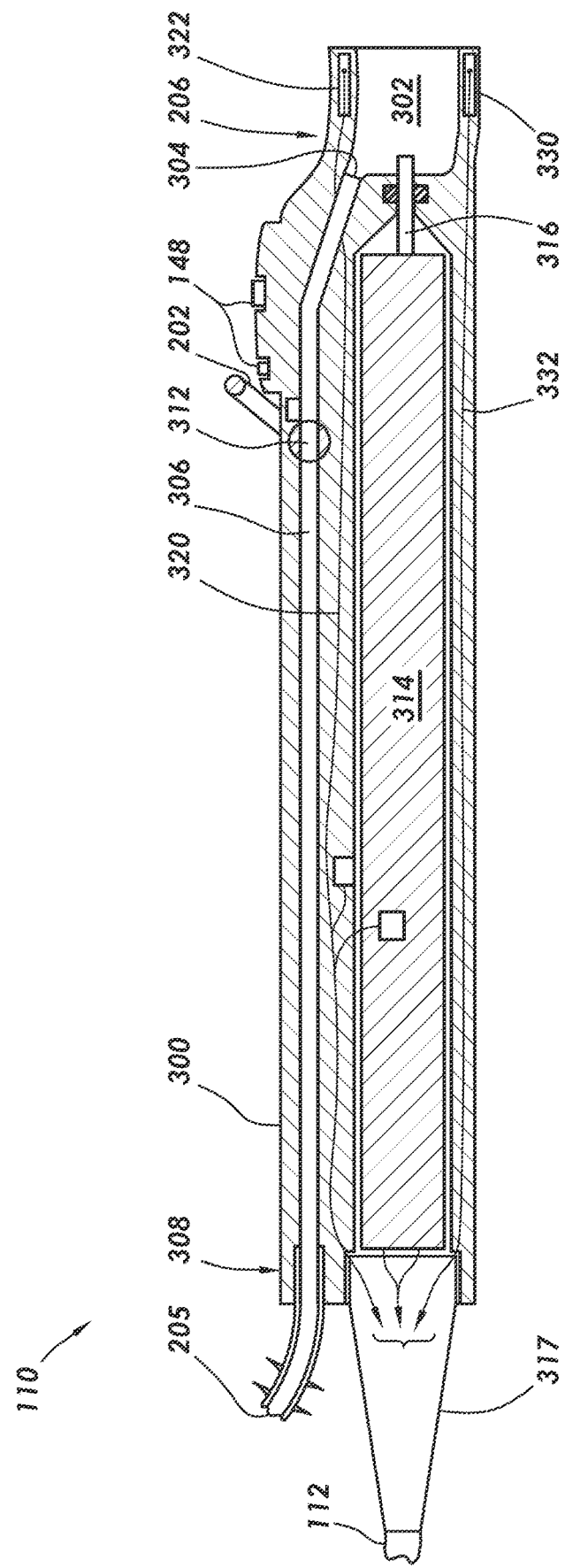
FIG. 3 shows a cross-sectional view of the motor drive unit (MDU) in accordance with at least some embodiments.

FIG. 3 shows a cross-sectional view of the MDU 110 in accordance with at least some embodiments. In particular, the example MDU 110 comprises an outer casing 300 that defines an outside surface where the surgeon grips the MDU 110 during surgical procedures. Exposed on the outside surface of the outer casing 300 are the buttons 148 discussed above. The distal end 206 of the MDU 110 includes a receptacle 302 into which the outer hub 204 (FIG. 2) is inserted when the mechanical resection instrument 104 (FIGS. 1 and 2) is mated with the MDU 110. In the example system, the receptacle 302 and outer hub 204 are constructed such that the outer hub 204 telescopes into the inside diameter of the receptacle 302, but any coupling mechanism may be used (e.g., the outer hub telescopes over the distal end 206 of the MDU 110). Within the receptacle 302 is defined a hole or aperture 304 that leads to the flow channel 306 through the MDU 110. At the proximal end 308 of the MDU 110 resides a hose connector 205 that is fluidly coupled to the flow channel 306. The hose connector 205 enables connection to the flexible tubular member 122 (FIG. 1).

FIG. 3 also shows the suction lever 202 rotationally coupled to the outside surface of the outer casing 300 of the MDU 110. The suction lever 202 is rigidly coupled to an example internal valve member 312 in operational relationship with the flow channel 306. In one rotational orientation of the suction lever 202 and thus valve member 312, and as shown in FIG. 3, the valve member 312 presents no impediment to the flow of the fluids and/or resection byproducts through the flow channel 306. In a second rotational orientation of the suction lever 202 and thus valve member 312 (the second rotational orientation not specifically shown), the valve member 312 may be oriented such that some impediment to the flow of the fluids and/or resection byproducts through the flow channel 306 is present.

The example MDU 110 further comprises a motor 314 that defines a drive shaft 316. The motor 314 is disposed within the outer casing 300 of the MDU 110, and the drive shaft 316 is exposed within the receptacle 302. When an outer hub 204 (not shown in FIG. 3) of a mechanical resection instrument 104 is coupled to the MDU 110, the rotating portion of the mechanical resection instrument (e.g., the inner hub and the inner tube) is mechanically coupled to the drive shaft 316 such that the motor 314 can control rotation of the rotating portion. The motor 314 may take any suitable form, such as a brushless Direct Current (DC) motor, stepper motor, Alternating Current (AC) motor, or even a pneumatic motor. While FIG. 3 shows the drive shaft 316 extending into the receptacle 302 for direct coupling to the inner hub of the mechanical resection instrument, in other cases various gears may be disposed between the drive shaft 316 and the rotating portion of the mechanical resection instrument to set the relationship between drive shaft 316 rotational speed and rotational speed of the rotating portion of the mechanical resection instrument. Assuming the motor 314 is an electrical motor for purposes of the further disclosure, electrical leads that couple to windings of the motor 314 feed through the connector 317 and into the flexible multi-conductor cable 112.

The motor 314 may operate in several different rotational modes. For example, one rotational mode is a forward rotation mode, where the motor 314 turns the rotating portion of the mechanical resection instrument in a single and continuous rotational direction. The forward rotation mode may be used for engaging specific cutting surfaces of a blade-type device with the tissue. Another example rotational mode may be a reverse rotation mode, where the motor 314 turns the rotating portion of the mechanical resection instrument in a direction opposite the forward rotation mode. The reverse rotation mode may be used for engaging different specific cutting surfaces of a blade-type device (e.g., the cutting surface on the opposite side of the cutting window of a blade-type device). Yet still another example rotational mode is an oscillation mode in which the motor (and thus the rotating portion) oscillates back and forth about a particular rotational orientation. For example, for a blade-type device the particular rotational position may be alignment of the cutting window of the outer tube (i.e., outer window) and the cutting window of the inner tube (i.e., inner window). Thus, by rotating in a first direction, a first cutting surface of the outer window engages with a first cutting surface of the inner window, and then by rotating in a second direction opposite the first direction, a second cutting surface of the outer window engages with a second cutting surface on the inner window. Other modes, and sub-modes, are possible. For example, within one of the continuous modes (e.g., forward or reverse), the speed of the rotation may be controlled. For example, in the forward mode the speed may slow when the inner window aligns with the outer window to provide time for the suction or aspiration to draw in tissue, and then the speed increases to provide crisp cutting action as between the cutting surfaces. Some of the rotational modes, and speeds, may be dependent upon the specific mechanical resection instrument used by the surgeon, and thus in some cases the MDU 110 and resection control unit 116 (FIG. 1) may be able to determine parameters associated with a mechanical resection instrument coupled to the MDU 110.

In accordance with example embodiments, the MDU 110 further comprises one or more magnetic field sensors in operational relationship to the receptacle 302. In the example MDU 110 of FIG. 3, two magnetic field sensors in the example form of Hall-effect sensors are used, one Hall-effect sensor 322 on an "upper" side of the MDU 110 (e.g., on the same side as the buttons 148), and one Hall-effect sensor 330 on the "bottom" side, opposite the upper side. The example Hall-effect sensor 322 is coupled to the resection control unit 116 by way of the leads 320. While the example Hall-effect sensor 322 is shown disposed in a side wall of the receptacle 302, the Hall-effect sensor 322 may be placed at any suitable location for reading magnetic field strength associated with magnets of the mechanical resection instrument, as discussed more below. Similarly, the Hall-effect sensor 330 is coupled to the resection control unit 116 by way of the leads 332. While the example Hall-effect sensor 330 is shown disposed in a side wall of the receptacle 302, the Hall-effect sensor 330 may be placed at any suitable location for reading magnetic field strength associated with the magnets of the mechanical resection instrument. In the example case of MDU 110 of FIG. 3, the Hall-effect sensors 322 and 330 are placed on opposite sides of the receptacle 302 (e.g., 180 rotational degrees apart relative to the long central axis of the MDU 110), but such placement is not strictly required. The example Hall-effect sensors may be closer together (e.g., between and including 90 and 180 rotational degrees) if desired. Moreover, while two Hall-effect sensors 322 and 330 are shown, one or more Hall-effect sensors may be used.

Each Hall-effect sensor 322 and 330 is a magnetic field sensor that produces a voltage output proportional to the magnetic field strength in proximity of the sensor. Many times in the related art the Hall-effect sensors are used in Boolean sense—determining merely the presence or absence of a magnet in proximity to the Hall-effect sensor. In example embodiments of this disclosure, however, the voltage output of each Hall-effect sensor is used in an analog sense. That is, a voltage output from one or both Hall-effect sensors may not only indicate the presence of a mechanical resection instrument, but the magnitude of the voltage output may also convey certain information. Moreover, and as discussed more below, one or both the Hall-effect sensors 322 and 330 may sense a combined magnetic field strength of two magnets associated with the mechanical resection instrument. The specification now turn to an example mechanical resection instrument.

Figure 4A:
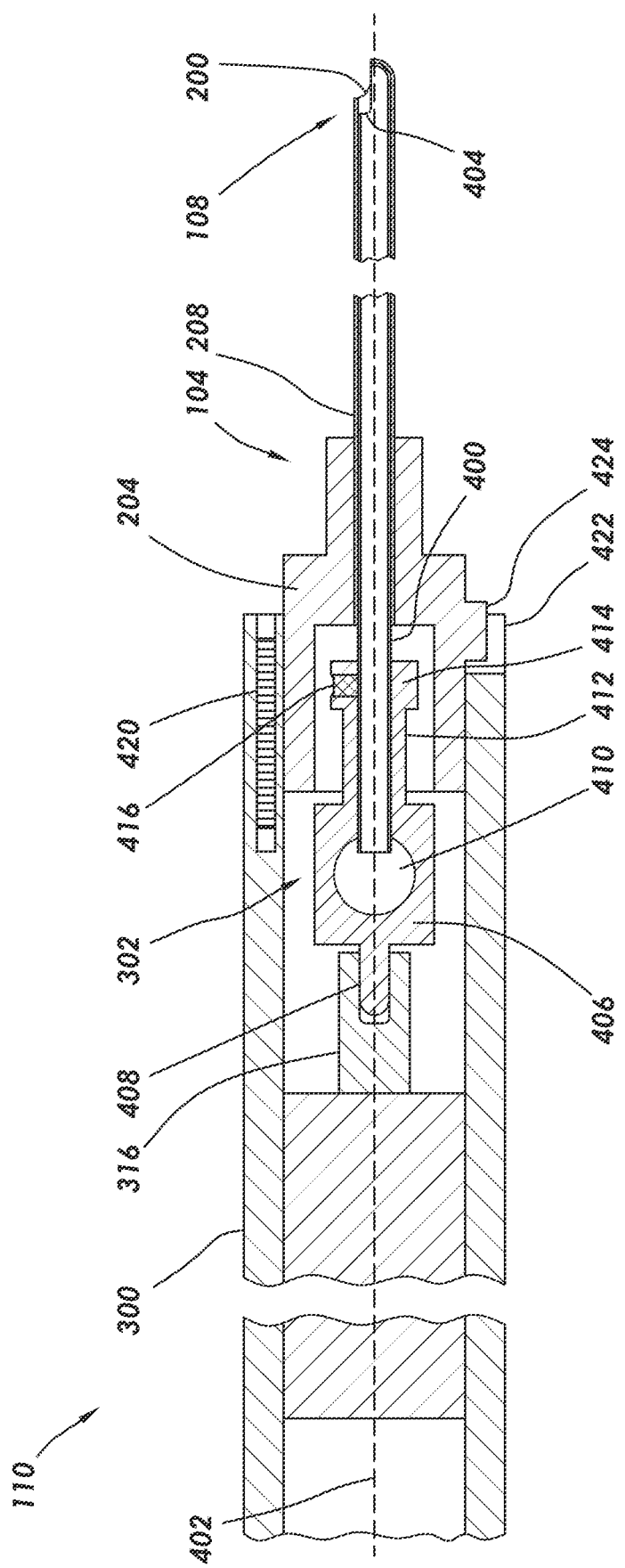
FIG. 4A shows a simplified side elevation, cross-sectional, view of a wand in accordance with at least some embodiments.

FIG. 4A shows a simplified cross-sectional side-elevation view of an MDU 110 and attached mechanical resection instrument 104, in accordance with at least some embodiments. In particular, FIG. 4A shows a portion of the outer casing 300 that defines the receptacle 302. The receptacle 302 defines an inside diameter into which the example outer hub 204 is telescoped. The outer hub 204 is rigidly coupled to the outer tube 208, and the outer tube 208 includes the cutting window 200 on the distal end 108. The example mechanical resection instrument 104 further includes an inner tube 400 concentrically disposed within the outer tube 208. The inner tube 400 and outer tube 208 share a longitudinal central axis 402, and in the example cases the longitudinal central axis 402 is also coaxial with the longitudinal central axis of the drive shaft 316 of the MDU 110. The inner tube 400 likewise defines a cutting window 404, and in the view of FIG. 4 the cutting window 404 of the inner tube 400 is aligned with the cutting window 200 of the outer tube 208. In particular, in the view of FIG. 4A the cutting window 404 of the inner tube 400 is fully aligned with the cutting window 200 of the outer tube 208 such that the effective size of the aperture into the inside diameter of the of the inner tube 400 is at its peak.

On the proximal end of the mechanical resection instrument 104 resides an inner hub 406 disposed at least partially within an inside diameter of the outer hub 204. The inner hub 406 is rigidly coupled to the inner tube 400 such that rotation of the inner hub 406 about the longitudinal central axis 402 likewise rotates the inner tube 400 about the longitudinal central axis 402. The example inner hub 406 defines a connector or coupler 408, a rotating slough chamber 410, and a magnet holder portion 412. The coupler 408 is in the example form a tab or tang that fits within a slot defined by the drive shaft 316. In other cases, a separate connector or coupler (not specifically shown) may couple to the drive shaft 316 and define the slot into which the tang projects. By way of the slot and coupler 408, the motor 314 turns the inner hub 406 and thus turns the inner tube 400 relative to the outer tube 208. The inner tube 400 has an inside diameter that defines a lumen fluidly coupled between the rotating slough chamber 410 and the cutting window 404 of the inner tube 400. Fluid and resection byproducts may thus be drawn through the cutting window 404, through the inside diameter of the inner tube 400, through the rotating slough chamber 410, and then through the flow channel 306 (not shown in FIG. 4) of the MDU 110.

The example magnet holder portion 412 includes a flange 414 that defines a bore into which a magnet 416 is placed. In some cases the bore into which the magnet 416 is placed is a blind bore such that the bore does not extend all the way through the flange 414. In one example case, the blind bore defines an aperture that is accessible on an outside surface of the flange 414. In another case, the bore is through bore that extends fully through the flange 414 of the magnet holder portion 412, though the inside portion may be mechanically blocked by the inner tube 400. The magnet 416 is held in its bore in any suitable way. For example, the magnet 416 may have an outside diameter selected to be a press-fit within the inside diameter of its respective bore. In other cases, the magnet 416 may be held in place by use of an adhesive. In one example case, the flange 414 may be omitted and the magnet 416 may be adhered directly to the outer surface of the magnet holder portion 412. Moreover, the magnet 416 may take any suitable shape without regard to the shape of the bore. For example, the magnet 416 may have an oblong or cylindrical shape with a long dimension that is parallel to the longitudinal central axis 402.

Still referring to FIG. 4A, visible within the sidewall that defines the receptacle 302 is a magnetic field sensor 420 that is representative of either Hall-effect sensor 322 or Hall-effect sensor 330 of FIG. 3. On the opposite side of the MDU 110 from the magnetic field sensor 420 is a slot 422. The slot 422 defines an open end that opens toward the distal end 108 of the wand 102, and the slot 422 defines a closed end proximal of the open end. In some example embodiments, the MDU 110 has two slots on opposite sides of the receptacle 302. Each slot defines an orientation in which the outer hub 204 may couple to the MDU 110. In accordance with example embodiments, the MDU 110 has a Hall-effect sensor associated with each slot. For example, if the distal end of the MDU 110 has two slots, then there will be at least two Hall-effect sensors, one Hall-effect sensor associated with each slot. In some cases, and as shown, the Hall-effect sensor associated with a slot may be on an opposite side of the receptacle 302 from the slot.

Relatedly, the example outer hub 204 defines a protrusion or tab 424 that extends outward from an outside surface of the outer hub 204. When the outer hub 204 is telescoped within the receptacle 302, the tab 424 telescopes within the slot 422. For an example MDU 110 that has two slots, it follows that the outer hub 204 may telescope into the receptacle 302 in one of two distinct rotational orientations about the longitudinal central axis 402.

In accordance with example embodiments the resection control unit 116 is designed and constructed to sense, by way of the representative magnetic field sensor 420, a magnetic field strength of the magnet 416 coupled to the inner hub 406, and determine a location of the cutting window 404 of the inner tube 400 based on the first magnetic field strength. Consider, for example, that at an instant in time at which the magnet 416 is the position shown in FIG. 4A, the resection control unit 116 reads the voltage output of the magnetic field sensor 420. In such a configuration, the magnetic field strength read by the magnetic field sensor 420 will be at its highest value. By contrast, after the inner hub 406 turns 180 rotational degrees, the magnetic field strength read by the magnetic field sensor 420 will be at its lowest value. The resection control unit 116 may determine the location of the cutting window 404 of the inner tube 400 based on the voltage output of the magnetic field sensor 420. In the configuration shown in FIG. 4A with the magnet 416 residing at the same radial position as the cutting window 404 of the inner tube 400, the resection control unit 116 may determine the location of the cutting window based on the peak magnetic field strength read. Oppositely, if the magnet 416 resides at a radial position 180 rotational degrees from the cutting window 404 (the relationship not specifically shown in FIG. 4A), the resection control unit 116 may determine the location of the cutting window based on the lowest magnetic field strength read.

In accordance with example embodiments, the resection control unit 116 is designed and constructed to use the information regarding the orientation of the cutting window 404 to control cutting window placement during operation. For example, with the orientation determined, the resection control unit 116 may implement the oscillation mode moving back and forth about the fully aligned window positions. As another example, the resection control unit 116 may be designed and constructed to implement rotational speed control of the inner hub 406 and inner tube 400 to implement crisp cutting action. In particular, in example embodiments the outer hub 204 may couple to the MDU 110 in one of two distinct orientations, one orientation associated with each slot (e.g., slot 422). The resection control unit 116 may be informed about the position of the cutting window 200 (such as by way of buttons 134), and thereafter the resection control unit 116 may slow the rotational speed of the inner tube 400 when the cutting windows are near the fully aligned orientation (e.g., to enable drawing in of tissue to be resected), and then accelerate as the respective cutting surfaces approach one another to implement the crisp cutting action.

In yet still other cases, the resection control unit 116 may be designed and constructed to stop the rotation of the inner tube 400 relative to the outer tube 208 with the cutting windows in a predetermined orientation. Again assuming the resection control unit 116 is informed about the location of the cutting window 200 of the outer tube 208, when the surgeon communicates an intent to stop rotation (e.g., releasing a foot switch, or releasing a switch on the MDU 110), the resection control unit 116 may stop the rotation of the inner tube 400 based on the magnetic field strength sensed. In some cases, the stopping is based in each case on reading magnetic field strength (e.g., the sensed value is a continuous position feedback to the resection control unit 116). In other cases, the resection control unit 116 may initially determine the position of the cutting window 404 using the magnetic field sensor 420, and thereafter track the relative orientations based on motor shaft position (e.g., measured or calculated), without further reference to the combined magnetic field strength.

Moreover, the relative orientation of the cutting windows when rotation is stopped may take many forms. For example, the resection control unit 116 may stop the rotation with the cutting window 200 of the outer tube 208 misaligned with the cutting window 404 of the inner tube 400. The resection control unit 116 may stop the rotation with the cutting window 200 of the outer tube 208 aligned with the cutting window 404 of the inner tube 400, in some cases fully aligned. The resection control unit 116 may stop the rotation with the cutting window 200 of the outer tube 208 blocked by the inner tube 400.

In some cases, the resection control unit 116 may determine an additional parameter from the magnitude of the magnetic field strength, such as identity of the mechanical resection instrument 104, rotational mode of the mechanical resection instrument 104 (e.g., forward rotation mode, reverse rotational mode oscillation mode), and designed speed of the rotation, to name a few.

Having a resection control unit 116 read a magnet associated with the inner hub 406 of a mechanical resection instrument as part of window alignment control provides many advantages over related-art systems in which no magnet is provided or associated with the inner hub 406. However, as alluded to above, even though the cutting window 200 may take only distinct radial positions (e.g., two distinct radial positions), in order to get precise window alignment the resection control unit 116 is informed about the position, a step which some surgeons will not take the time to complete. Thus, in yet still further embodiments the radial location of the cutting window 200 through the outer tube 208 is also identified by a magnet.

Figure 4B:
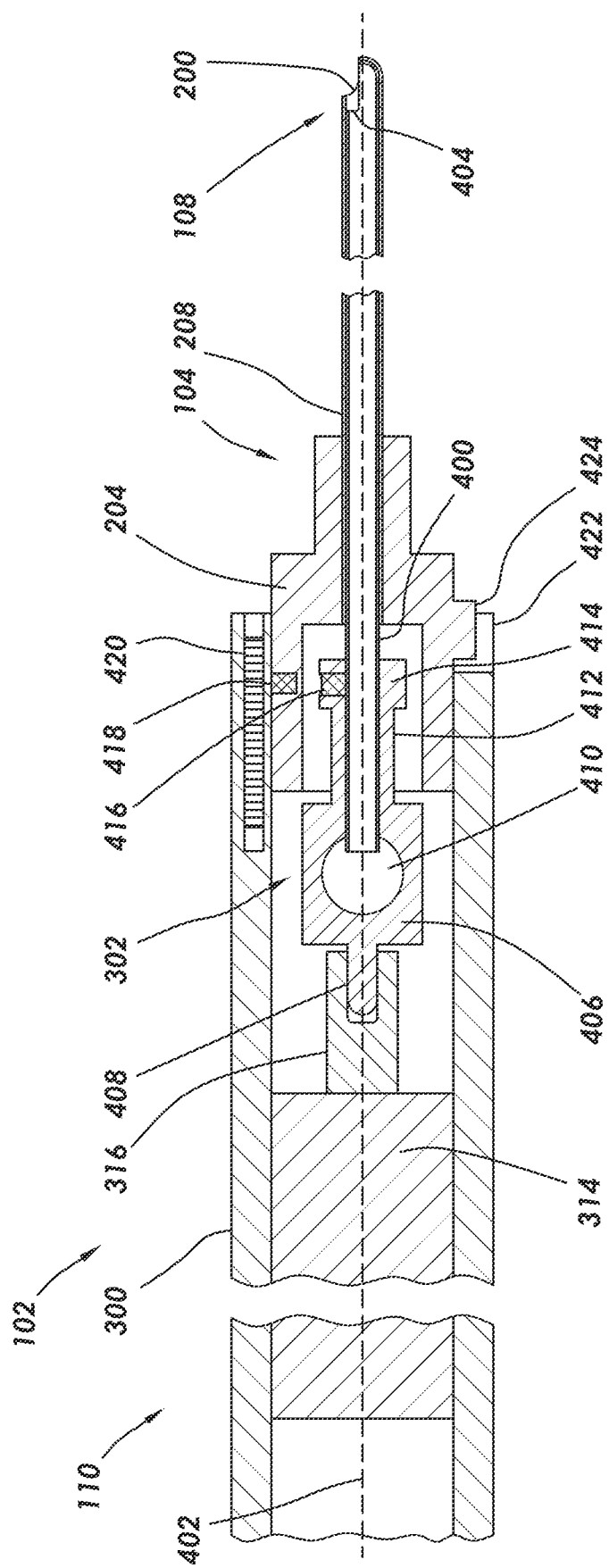
FIG. 4B shows a simplified side elevation, cross-sectional, view of a wand in accordance with at least some embodiments.

FIG. 4B shows a simplified cross-sectional side-elevation view of an MDU 110 and attached mechanical resection instrument 104, in accordance with at least some embodiments. Most the components shown in FIG. 4B are duplicative of those described in FIG. 4A, and perform the same function, and thus the components carry the same reference numbers but are not described again so as not to unduly lengthen the specification. In particular, FIG. 4B shows the outer hub 204 defines a bore into which a magnet 418 is placed. In some cases the bore into which the magnet 418 is placed is a blind bore such that the bore does not extend all the way through the outer hub 204. In some cases, the blind bore for the magnet 418 defines an aperture that is accessible on an outside surface of the outer hub 204. In other cases, the blind bore for the magnet 418 defines an aperture on an inside surface of the outer hub 204. In yet still other cases, the bore is through bore that extends fully through the outer hub 204 of the magnet holder portion 412.

The magnet 418 is held in its bores in any suitable way. For example, the magnet 418 may have an outside diameter selected to be a press-fit within the inside diameter of the bore. In other cases, the magnet 418 may be held in by use of an adhesive. In the case of the magnet 418, if there is sufficient space within the outer hub 204 between the inside diameter of the outer hub 204 and the outside diameter of the magnet holder portion 412 of the inner hub 406, the magnet 418 may be adhered to the inside diameter of the outer hub 204 and thus not reside within a bore.

In the example system, when the mechanical resection instrument 104 is coupled to the MDU 110, the magnet 416 and the magnet 418 are at the same axial location along the longitudinal central axis 402. In other cases, the magnets 416 and 418 may be offset from one another along the longitudinal central axis 402, yet still close enough that their respective magnetic fields interact in relation to at least one Hall-effect sensor. In cases in which there is offset between the magnets 416 and 418, with the offset may be between and including 1 millimeter (mm) and 5 mm. Moreover, the discussion to this point has assumed the magnet 418 to be of a cylindrical shape to telescope within a circular bore; however, in other cases the bore may take any suitable shape (e.g., oblong). Moreover, the magnet 418 may take any suitable shape without regard to the shape of the bore. For example, the magnet 418 may have an oblong or cylindrical shape with a long dimension that is parallel to the longitudinal central axis 402.

Still referring to FIG. 4B, as before the sidewall that defines the receptacle 302 hosts the magnetic field sensor 420 that is representative of either Hall-effect sensor 322 or Hall-effect sensor 330 of FIG. 3. On the opposite side of the MDU 110 from the magnetic field sensor 420 is the slot 422. Again as before, the example outer hub 204 defines a protrusion or tab 424 that extends outward from an outside surface of the outer hub 204. When the outer hub 204 is telescoped within the receptacle 302, the tab 424 telescopes within the slot 422. For an example MDU 110 that has two slots, it follows that the outer hub 204 may telescope into the receptacle 302 in one of two distinct rotational orientations about the longitudinal central axis 402. In example embodiments, the radial location of the tab 424 relative to the longitudinal central axis 402 of the mechanical resection instrument 104 is designed and constructed to place the magnet 418 associated with the outer hub 204 proximate to the location of the associated Hall-effect sensor. In the example of FIG. 4, the slot 422 places the magnet 418 proximate to the representative magnetic field sensor 420. While FIG. 4B shows the tab 424 residing at a radial location opposite that of the magnet 418 (e.g., at a radial 180 rotational degrees offset), the magnet 418 may be placed at any suitable rotational offset relative to the tab 424, including locations in which the magnet 418 is at the same radial location relative to the longitudinal central axis 402.

Figure 5A:
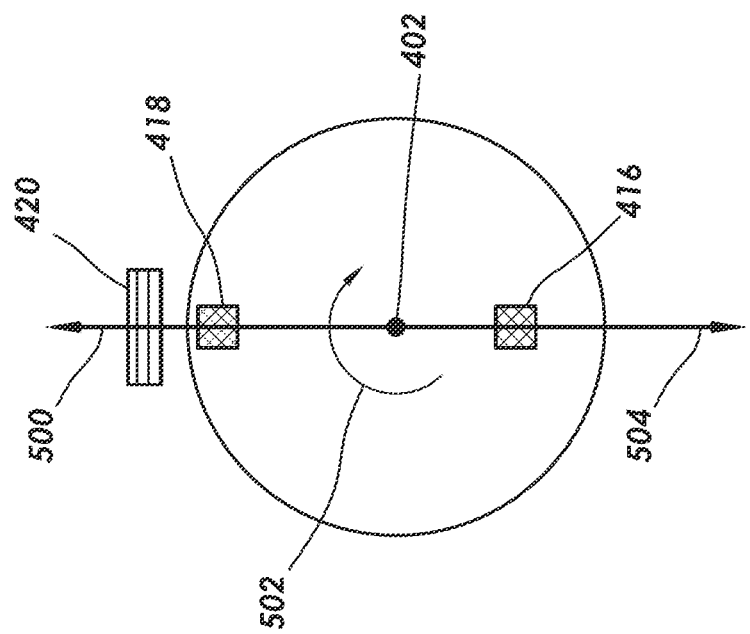
FIG. 5A shows a simplified elevation view of the magnets and magnetic field sensor looking along the longitudinal central axis, in accordance with at least some embodiments.

FIG. 5A shows a simplified elevation view of the magnets and magnetic field sensor, the view looking along the longitudinal central axis 402, and in accordance with at least some embodiments. In particular, FIG. 5A shows the magnet 416 associated with the inner hub 406, the magnet 418 associated with the outer hub 204, and the representative magnetic field sensor 420 all residing on the same radial 500 relative to the longitudinal central axis 402. In the view of FIG. 5A, the longitudinal central axis 402 is perpendicular to the plane of the page, and thus is shown as a point.

In operation, the MDU 110 turns the inner hub 406 about the longitudinal central axis 402. Consider for purposes of explanation that the direction of rotation of the inner hub 406 is shown by the arrow 502 in FIG. 5A. Thus, when the MDU 110 is turning the inner hub 406, the magnet 416 associated with the inner hub 406 rotates around the longitudinal central axis 402 in an example direction shown by arrow 502.

Figure 5B:
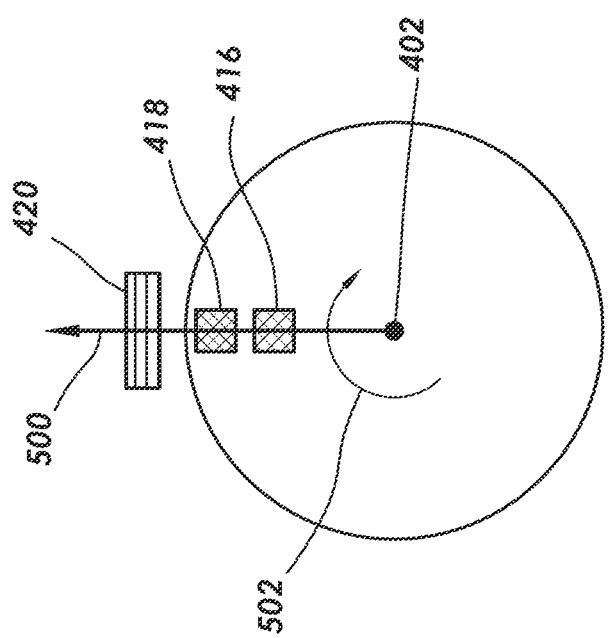
FIG. 5B shows a simplified elevation view of the magnets and magnetic field sensor, the view looking along the longitudinal central axis, after rotation, and in accordance with at least some embodiments.

FIG. 5B shows a simplified elevation view of the magnets and magnetic field sensor, the view looking along the longitudinal central axis 402, after rotation of the inner hub 406 by one-half a turn, and in accordance with at least some embodiments. In particular, FIG. 5B again shows the magnet 416 associated with the inner hub 406, the magnet 418 associated with the outer hub 204, and the representative magnetic field sensor 420. In FIG. 5B, however, while the magnetic field sensor 420 and the magnet 418 associated with the outer hub 204 still reside along the radial 500, in the example situation of FIG. 5B the magnet 416 associated with the inner hub 406 has rotated 180 rotational degrees and thus resides along radial 504. Thus, as the motor 314 and drive shaft 316 turn the inner hub 406 about the longitudinal central axis 402, the magnet 416 travels a circular path, at certain points in time residing along a shared radial 500 with the respect to the magnet 418, and at other points in time residing along a radial 504 that is 180 rotational degrees from the radial 500.

Referring simultaneously to FIGS. 4B, 5A, and 5B, in accordance with example embodiments the resection control unit 116 is designed and constructed to sense, by way of the representative magnetic field sensor 420, a magnetic field strength of the magnet 418 coupled to the outer hub 204, and determine a location of the cutting window 200 of the outer tube 208 based on the first magnetic field strength. Consider, for example, that at the instant in time at which the magnets are in the positions shown in FIG. 5B, the resection control unit 116 reads the voltage output of the magnetic field sensor 420. In such a configuration, the magnetic field strength read by the magnetic field sensor 420 will be predominately, if not exclusively, the magnetic field strength of the magnet 418. Based on the magnetic field strength at the instant represented by FIG. 5B, the resection control unit 116 may determine the location of the cutting window 200 of the outer tube 208 based on the voltage output of the magnetic field sensor 420. In some cases, the resection control unit 116 may determine an additional parameter from the magnitude of the magnetic field strength, such as identity of the mechanical resection instrument 104, rotational mode of the mechanical resection instrument 104 (e.g., forward rotation mode, reverse rotational mode oscillation mode), and designed speed of the rotation, to name a few.

The resection control unit 116 is further designed and constructed to sense, by way of the representative magnetic field sensor 420, a combined magnetic field strength of the magnet 416 and the magnet 418. Based on the combined magnetic field strength, the resection control unit 116 may determine a location of the cutting window 200 of the outer tube 208. Consider, for example, that at the instant in time at which the magnets are in the positions shown in FIG. 5A, the resection control unit 116 reads the voltage output of the magnetic field sensor 420. In such a configuration, the magnetic field strength read by the magnetic field sensor 420 will be the combined magnetic field strength of the magnet 416 and the magnet 418. Based on the combined magnetic field strength at the instant in time represented by FIG. 5A, the resection control unit 116 may determine the location of the cutting window 404 of the inner tube 400 based on the voltage output of the magnetic field sensor 420. In some cases, the resection control unit 116 may determine an additional parameter from the combined magnitude of the magnetic field strength, such as any one of the parameters noted above that is not otherwise identified by the magnetic field strength of the magnet 418 alone.

The magnets shown in FIGS. 5A and 5B may be placed at their respective locations with their respective magnetic fields aligned in multiple orientations or polarities. For example, magnet 418 associated with the outer hub 204 may have its magnetic North closer to or facing the magnetic field sensor 420, or magnet 418 may have its magnetic South closer to or facing the magnetic field sensor 420. Stated oppositely, magnet 418 associated with the outer hub 204 may have its magnetic South closer to or facing the longitudinal central axis 402, or magnet 418 may have its magnetic North closer to or facing the longitudinal central axis 402.

Similarly, magnet 416 associated with the inner hub 406 may have its magnetic South closer to or facing the longitudinal central axis 402, or magnet 416 may have its magnetic North closer to or facing the longitudinal central axis 402. It follows that sensing the magnetic field strength may take many forms. For example, sensing the magnetic field strength of the magnet 418 may comprise sensing a first magnitude with a first polarity, and sensing the combined magnetic field strength may comprise: sensing a second magnitude higher than the first magnitude and with the first polarity (e.g., when the polarities are aligned in the configuration of FIG. 5A); sensing a second magnitude lower than the first magnitude and with the first polarity (e.g., when the polarities are arranged oppositely, yet the magnetic field strength of the magnet 416 is the same or lower than the magnetic field strength of the magnet 418); and sensing a second magnitude with a second polarity opposite the first polarity (e.g., when the polarities are arranged oppositely, and the magnetic field strength of the magnet 416 is the greater than the magnetic field strength of the magnet 418).

Returning to FIG. 1. In accordance with example embodiments, the resection control unit 116 is designed and constructed to use the information regarding the relative orientations of the cutting windows to control cutting window placement during operation. For example, with the relative orientations determined, the resection control unit 116 may implement the oscillation mode moving back and forth about the fully aligned window positions. As another example, the resection control unit 116 may be designed and constructed to implement rotational speed control of the inner hub 406 and inner tube 400 to implement crisp cutting action. More particularly, the resection control unit 116 may slow the rotational speed of the inner tube 400 when the cutting windows are near the fully aligned orientation (e.g., to enable drawing in of tissue to be resected), and then accelerate as the respective cutting surfaces approach one another to implement the crisp cutting action.

In yet still other cases, the resection control unit 116 may be designed and constructed to sense the relative locations of the cutting window 200 of the outer tube 208 and the cutting window 404 of the inner tube 400, and stop the rotation of the inner tube 400 relative to the outer tube 208 with the cutting windows in a predetermined orientation. For example, when the surgeon communicates an intent to stop rotation (e.g., releasing a foot switch, or releasing a switch on the MDU 110), the resection control unit 116 may stop the rotation of the inner tube 400 based on the combined magnetic field strength sensed. In some cases, the stopping in every case based on the reading combined magnetic field strength (e.g., the sensed value is a continuous position feedback to the resection control unit 116). In other cases, the resection control unit 116 may initially read the relative orientation, and thereafter track the relative orientations based on motor shaft position (e.g., measured or calculated), without further reference to the combined magnetic field strength.

Moreover, the relative orientation of the cutting windows when rotation is stopped may take many forms. For example, the resection control unit 116 may stop the rotation with the cutting window 200 of the outer tube 208 misaligned with the cutting window 404 of the inner tube 400. The resection control unit 116 may stop the rotation with the cutting window 200 of the outer tube 208 aligned with the cutting window 404 of the inner tube 400, in some cases fully aligned. The resection control unit 116 may stop the rotation with the cutting window 200 of the outer tube 208 blocked by the inner tube 400.

Figure 6:
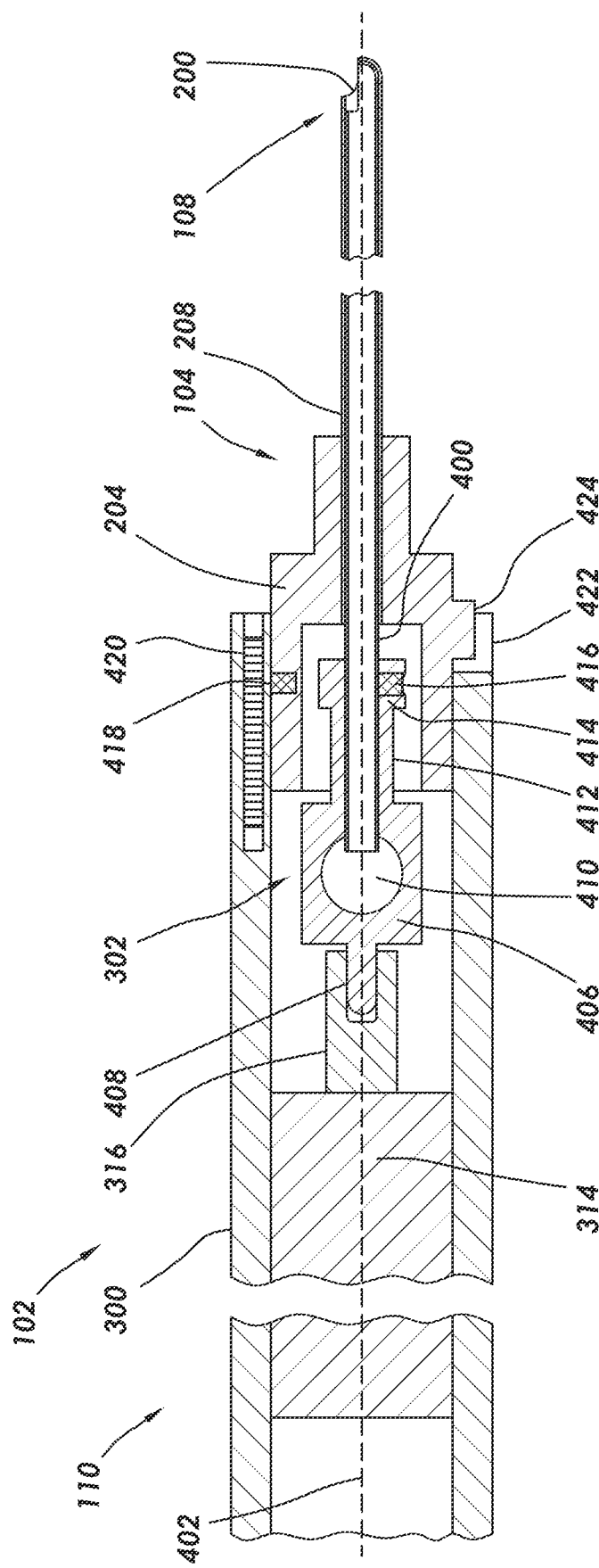
FIG. 6 shows a simplified side elevation, cross-sectional, view of a wand in accordance with at least some embodiments.

FIG. 6 shows a simplified cross-sectional side-elevation view of an MDU 110 and attached mechanical resection instrument 104, in accordance with at least some embodiments. In particular, FIG. 6 shows a stopped orientation where the cutting window 200 of the outer tube 208 is fully blocked by the inner tube 400. Note also the example orientation of the magnet 416 when cutting window 200 of the outer tube 208 is fully blocked by the inner tube 400. The arrangement of FIG. 6 is merely an example, and the rotational position of magnet 416 relative to the cutting window of the inner tube 400 may take any suitable form. For example, and as shown, the magnet 416 may be 180 rotational degrees from the magnet 418 when the inner tube 400 block the cutting window 200 of the outer tube 208. In other cases, the magnets 416 and 418 may reside along same radial (e.g., FIG. 5A) when the inner tube 400 block the cutting window 200 of the outer tube 208.

With the information derived from reading the magnetic field strengths, the resection control unit 116 can automatically stop the inner tube and outer tube in any orientation, without the user needing to calibrate or align the tubes. Such is an improvement over the related art in which the user was required to manually position the tubes for the stopped orientation (e.g., by repeatedly starting the stopping the rotation until the tubes stopped in the desired orientation).

The various embodiments discussed to this point have assumed a single magnet associated with the outer hub, a single magnet associated with the inner hub, and thus a single combined magnetic field strength. However, in other example cases the inner hub may have one or more magnets associated therewith. As each magnet of the inner hub resides along the same radial as the magnet of the outer hub, the magnetic field sensor may thus read multiple and distinct combined magnetic field strengths. Thus, the magnetic field strength of the magnet coupled to the outer hub may convey information, the first combined magnetic field strength may convey additional and non-duplicative information, and the third combined magnetic field strength may convey yet still further additional and non-duplicative information, and so on.

Figure 7:
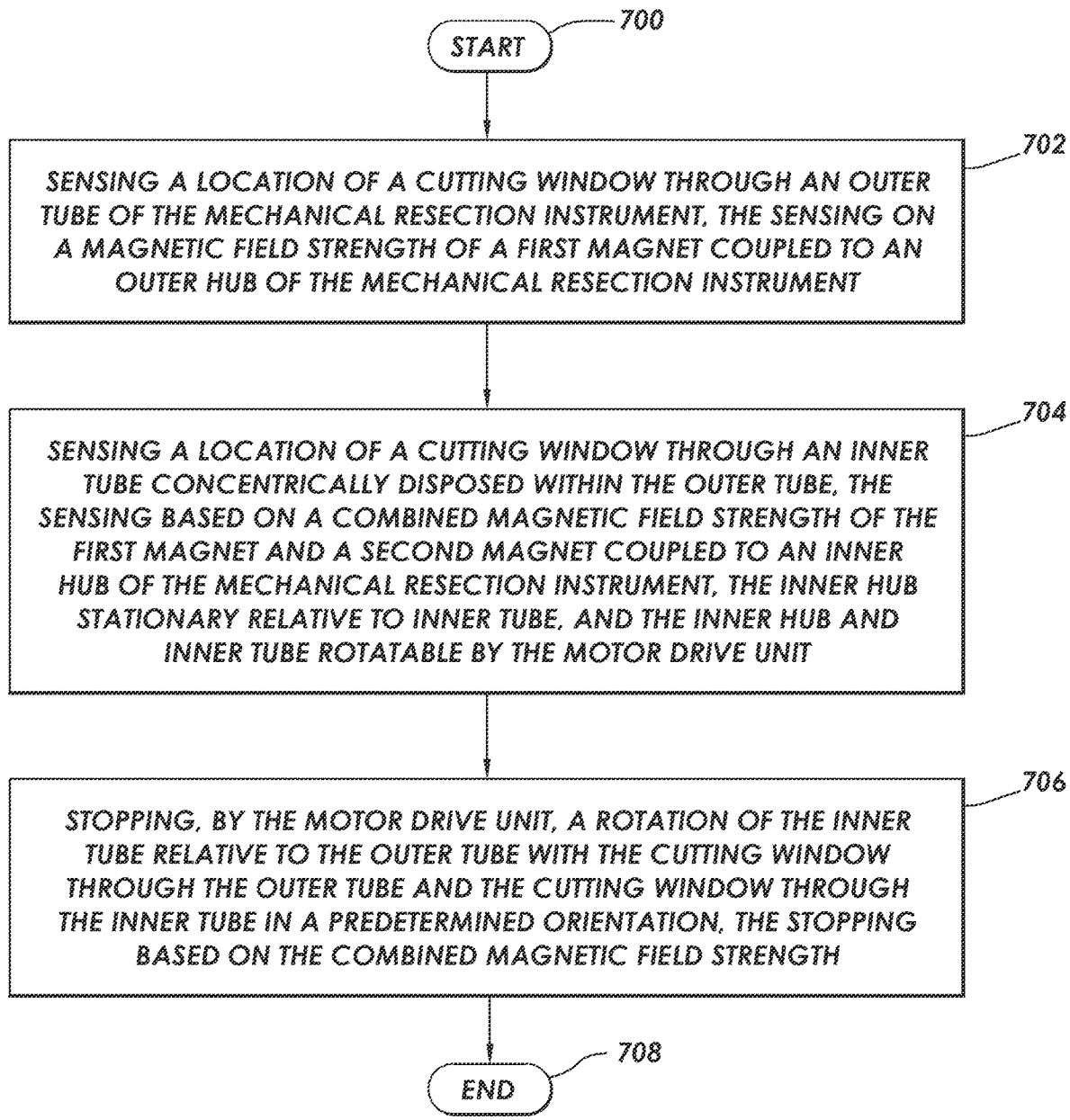
FIG. 7 shows a method in accordance with at least some embodiments.

FIG. 7 shows a method in accordance with at least some embodiments. In particular, the method starts (block 700) and comprises: sensing a location of a cutting window through an outer tube of the mechanical resection instrument, the sensing based on a magnetic field strength of a first magnet coupled to an outer hub of the mechanical resection instrument (block 702); sensing a location of a cutting window through an inner tube concentrically disposed within the outer tube, the sensing based on a combined magnetic field strength of the first magnet and a second magnet coupled to an inner hub of the mechanical resection instrument, the inner hub stationary relative to inner tube, and the inner hub and inner tube rotatable by the motor drive unit (block 704); and stopping, by the motor drive unit, a rotation of the inner tube relative to the outer tube with the cutting window through the outer tube and the cutting window through the inner tube in a predetermined orientation, the stopping based on the combined magnetic field strength (block 706). Thereafter, the method ends (block 708).

The above discussion is meant to be illustrative of the principles and various embodiments of the present invention. Numerous variations and modifications will become apparent to those skilled in the art once the above disclosure is fully appreciated. For example, while Hall-effect sensors are discussed as the example magnetic field sensors, any suitable sensor for sensing magnetic field strength may be used, such as fluxgate magnetometers and/or magnetoresistance-based devices. In the case of the embodiments with one or more magnets coupled to the inner hub, the outer hub may have no magnets and/or no metallic materials to channel or direct magnetic field in the vicinity of the magnet(s) on the inner hub. It is intended that the following claims be interpreted to embrace all such variations and modifications.

What is claimed is:

1. A method of operating a mechanical resection instrument coupled to a motor drive unit, the method comprising:
   sensing a location of a cutting window through an outer tube of the mechanical resection instrument, the sensing based on a magnetic field strength of a first magnet coupled to an outer hub of the mechanical resection instrument, wherein sensing the magnetic field strength of the first magnet further comprises sensing a first magnitude with a first polarity;
   sensing a location of a cutting window through an inner tube concentrically disposed within the outer tube, the sensing based on a combined magnetic field strength of the first magnet and a second magnet coupled to an inner hub of the mechanical resection instrument, the inner hub stationary relative to the inner tube, and the inner hub and the inner tube rotatable by the motor drive unit, wherein sensing the combined magnetic field strength further comprises at least one selected from a group comprising: sensing a second magnitude higher than the first magnitude and with the first polarity; sensing a second magnitude lower than the first magnitude and with the first polarity; sensing a second magnitude with a second polarity opposite the first polarity; and stopping, by the motor drive unit, a rotation of the inner tube relative to the outer tube with the cutting window through the outer tube and the cutting window through the inner tube in a predetermined orientation, the stopping based on the combined magnetic field strength.

2. The method of claim 1 wherein stopping the rotation of the inner tube relative to the outer tube further comprises stopping the rotation with the cutting window through the outer tube blocked by the inner tube.

3. The method of claim 1 wherein stopping the rotation of the inner tube relative to the outer tube further comprises stopping the rotation with the cutting window through the outer tube misaligned with the cutting window through by the inner tube.

4. The method of claim 1 wherein stopping the rotation of the inner tube relative to the outer tube further comprises stopping the rotation with the cutting window through the outer tube aligned with the cutting window through the inner tube.

5. The method of claim 1 further comprising reading, by the motor drive unit, a first parameter of the mechanical resection instrument based on the magnetic field strength of the first magnet alone.

6. The method of claim 5 further comprising reading, by the motor drive unit, a second parameter of the mechanical resection instrument based on the combined magnetic field strength.

7. A mechanical resection system comprising:
a motor drive unit comprising a motor and a magnetic field sensor in operational relationship to a hub connector;
a resection control unit communicatively coupled to the motor and the magnetic field sensor;
a resection instrument comprising:
an outer hub coupled to the hub connector, and an outer tube with a cutting window;
an inner hub coupled to a drive shaft of the motor, and an inner tube with a cutting window rigidly coupled to the inner hub, the inner tube concentrically disposed within the outer tube;
a first magnet coupled to the outer hub; and
a second magnet coupled to the inner hub;
the resection control unit configured to:
cause rotation of the drive shaft of the motor, and thereby rotate the inner hub and the inner tube relative to the motor drive unit, the rotation responsive to activation of a switch;
sense, by way of the magnetic field sensor, a first magnetic field strength of the first magnet coupled to the outer hub, and determine a location of the cutting window through the outer tube based on the first magnetic field strength, wherein sensing the first magnetic field strength of the first magnet further comprises sensing a first magnitude with a first polarity;
sense, by way of the magnetic field sensor, a combined magnetic field strength of the first magnet and the second magnet, and determine a location of the cutting window through the inner tube based on the combined magnetic field strength, wherein sensing the combined magnetic field strength further comprises at least one selected from a group comprising: sensing a second magnitude higher than the first magnitude and with the first polarity; sensing a second magnitude lower than the first magnitude and with the first polarity; sensing a second magnitude with a second polarity opposite the first polarity; and stop the rotation of the inner tube relative to the outer tube with the cutting window through the outer tube and the cutting window through the inner tube in a predetermined orientation, the stopping responsive to deactivation of the switch, and the predetermined orientation of the inner tube and output based on the combined magnetic field strength.

8. The mechanical resection system of claim 7 wherein when the resection control unit stops the rotation at the predetermined orientation, the resection control unit is further configured to stop the rotation with the cutting window through the outer tube blocked by the inner tube.

9. The mechanical resection system of claim 7 wherein when the resection control unit stops the rotation at the predetermined orientation, the resection control unit is further configured to stop the rotation with the cutting window through the outer tube misaligned with the cutting window through by the inner tube.

10. The mechanical resection system of claim 7 when the resection control unit stops the rotation at the predetermined orientation, the resection control unit is further configured to stop the rotation with the cutting window through the outer tube aligned with the cutting window through the inner tube.

11. The mechanical resection system of claim 7 wherein the resection control unit is further configured to read a first parameter of the resection instrument based on the first magnetic field strength of the first magnet alone.

12. The mechanical resection system of claim 11 wherein the resection control unit is further configured to read a second parameter of the resection instrument based on the combined magnetic field strength.

13. A mechanical resection instrument comprising:
an outer hub rigidly coupled to an outer tube, the outer tube defining a cutting window on a distal end thereof;
a first magnet coupled to the outer hub, a radial location of the first magnet about the outer hub indicative of location of the cutting window of the outer tube relative to the outer hub;
an inner hub coupled to an inner tube, the inner tube concentrically disposed within the outer tube, and the inner tube defining a cutting window on a distal end thereof;
a second magnet coupled to the inner hub, a radial location of the first magnet about the inner hub indicative of location of the cutting window of the inner tube relative to the inner hub;
a magnetic field strength of the first magnet indicative of a first parameter of the mechanical resection instrument, the magnetic field strength of the first magnet having a first magnitude with a first polarity;
a combined magnetic field strength of the first magnet and the second magnet, when the first magnet and the second magnet reside on a same radial, is indicative of a second parameter of the mechanical resection instrument, the combined magnetic field strength having at least one selected from a group comprising: a second magnitude higher than the first magnitude and with the first polarity; a second magnitude lower than the first magnitude and with the first polarity; a second magnitude with a second polarity opposite the first polarity.

14. The mechanical resection instrument of claim 13 wherein the magnetic field strength of the first magnet is indicative of at least one selected from a group comprising: an operating speed of the inner tube relative to the outer tube; an oscillation mode of the mechanical resection instrument; and identity of the mechanical resection instrument.

15. The mechanical resection instrument of claim 13 wherein the combined magnetic field strength is indicative of alignment of the cutting window of the outer tube with the cutting window of the inner tube.

16. The mechanical resection instrument of claim 13 further comprising a third magnet coupled to the inner hub, the third magnet distinct from the first and second magnets.

17. The mechanical resection instrument of claim 16 wherein a combined magnetic field strength of the first and third magnet is indicative of a third parameter of the mechanical resection instrument, the third parameter distinct from the first and second parameters.

\* \* \* \* \*